United States Patent [19]

Granlund

[11] 4,377,077
[45] Mar. 22, 1983

[54] DEVICE AND METHOD FOR CONTROLLED FREEZING OF CELL CULTURES

[75] Inventor: David J. Granlund, Rockville, Md.

[73] Assignee: Biotech Research Laboratories, Inc., Rockville, Md.

[21] Appl. No.: 283,634

[22] Filed: Jul. 15, 1981

[51] Int. Cl.³ .............................................. F25D 3/08
[52] U.S. Cl. ........................................ 62/457; 62/78; 435/284
[58] Field of Search ............... 62/78, 64, 457, 466, 62/371; 435/284

[56] References Cited

U.S. PATENT DOCUMENTS

| | | | |
|---|---|---|---|
| Re. 28,276 | 12/1974 | Farr | 195/96 |
| 1,681,110 | 8/1928 | Freidman | 62/457 |
| 2,024,648 | 12/1935 | Kissling et al. | 62/457 |
| 3,228,838 | 4/1959 | Rinfret et al. | 62/78 |
| 3,261,761 | 7/1966 | Anderson | 195/96 |
| 3,344,617 | 2/1965 | Rinfret et al. | 62/78 |
| 3,649,462 | 11/1969 | Jessup | 195/127 |
| 3,975,545 | 8/1976 | Vedamuthu | 426/40 |
| 4,018,585 | 4/1977 | Loratto | 62/457 |
| 4,060,457 | 11/1977 | Iizuka et al. | 195/127 |
| 4,226,940 | 10/1980 | Storrs | 435/260 |

OTHER PUBLICATIONS

"Instructions for BF-5 Biological Freezer", Form 11-361-B, Mar. 1975, pp. 1-4.
"Planer Mini-Freezer R202/200R", Advertising Literature, four pp., undated.

Primary Examiner—Ronald C. Capossela
Attorney, Agent, or Firm—Fleit, Jacobson & Cohn

[57] ABSTRACT

An enclosed device and method for controlled freezing of cell cultures, especially eucaryotic cell cultures, contained in cell culture vials by means of a conventional freezer includes a container and top, a supporting grid and supporting grid base within the container for supporting the cultire vials and a compatible liquid refrigerant in a volume of at least fifteen times the culture volume and at a level to totally immerse all of the cultures to be frozen. Compatible liquid refrigerants include the straight chain aliphatic alcohols, preferably ethanol and methanol.

15 Claims, 5 Drawing Figures

DEVICE AND METHOD FOR CONTROLLED FREEZING OF CELL CULTURES

FIELD OF INVENTION

This invention relates primarily to a novel and useful apparatus for obtaining a controlled freezing of concentrated cell cultures, particularly eucaryotic cells, in a conventional laboratory research freezer and secondarily to a method for controlling that freezing.

BACKGROUND OF THE INVENTION AND DESCRIPTION OF THE PRIOR ART

In recent years, it has become increasingly desirable and important in biological research to freeze cell cultures so that they may be stored in the frozen state until immediately prior to use because viability of the cells can thus be maintained for extended periods of time. This freezing and storage process contemplates that cell cultures at room temperatures of about $+20°$ C. be reduced in temperature to temperatures of at least $-30°$ C. or lower.

However, the freezing of such cultures is not without certain shortcomings. Cell cultures typically are suspended in a water based medium for growth and storage. As known in the art, cryogenic preservation and storage of cell cultures requires the inclusion of dimethyl sulfoxide or glycerol. When freezing this water based suspension to preserve the viability of the cells, damage can occur to the cells if there is a formation of ice crystals which can puncture or otherwise physically damage the cell walls. This potential problem can be minimized by rapidly freezing the culture. This rapid freezing promotes the formation of small ice crystals which generally do not cause as much damage to the cells as larger ice crystals, typically formed during slower freezing.

On the other hand, too abrupt a change in the physical state of the cells, as by too rapid a freezing of the culture, can destroy the cells to be stored or otherwise have an adverse effect on subsequent cell activity. Hence, it is generally recognized by those skilled in the art that optimum freezing of cell cultures, particularly eucaryotic cell cultures, from room temperature to at least $-30°$ C. or lower is achieved if the temperature of the cell culture decreases at a theoretical rate of approximately 1° C. per minute. Freezing at this theoretically preferred $-1°$ C./min. rate is generally recognized as the optimum temperature reduction for cryopreservation of live cells, especially eucaryotic cells. This optimum temperature reduction is most critical in the range of about $-4°$ C., when cultures begin crystal formations, to about $-25°$ C., where crystal formation is complete.

The equipment presently available to research biologists and others for freezing cell cultures is extremely expensive or unreliable in controlling the freezing of the cultures. One type equipment employs liquid nitrogen as the freezing medium and generally costs in excess of $10,000. One such device is manufactured by Planer Products Ltd. of Great Britain and identified as the Planer Mini-Freezer R202/200R. A much lower priced alternative device is manufactured by Union Carbide Corporation and is identified as the "BF-5 Biological Freezer". This device, however, has the distinct disadvantage of requiring the research scientist to correctly calibrate the position of the vial holder within the freezing compartment, depending on the number of individual cell cultures to be frozen. Such calibration often results in inconsistent freezing of the cultures.

In view of the extremely high cost of the only reliable presently available freezing equipment, individual research scientists have employed their own homemade controlling devices for use in their conventional laboratory freezers, which are normally operated at $-70°$ C. to $-90°$ C. Such homemade devices have included cotton wrapping around the cell culture vials which are then placed into a styrofoam box, or jars containing alcohol. However, these homemade devices have not been satisfactory since they produce inconsistent controlled freezing and generally fail to approach the desired theoretical optimum temperature reduction. Furthermore, they very often fail to maintain the proper orientation of the stored cell culture vials during the freezing process.

Accordingly, it is the principal object of this invention to provide a simple, inexpensive, but very reliable device for controlling the freezing of cell cultures in conventional laboratory freezers, especially eucaryotic cell cultures.

A further object of this invention is to provide a device for freezing cell cultures which approaches the optimum $-1°$ C./min. freezing rate which promotes the best preservation of viability of the live cells.

Another object resides in the novel supporting mechanism of the freeze controlling device by which the vials containing the cell cultures are easily and safely supported and stored within the device.

A still further important object of the present invention is to provide uniform temperature reduction of the cultures without variation or calibration of the device, regardless of the number of different cultures being frozen at the same time.

The final important object of this invention is to provide a method by which controlled freezing of live cell cultures can be easily and safely carried out in standard laboratory freezers operated at $-70°$ C., or below.

SUMMARY OF THE INVENTION

The foregoing objects are obtained in accordance with the present invention by a device which includes an open-topped container and lid in which is placed a supporting grid and supporting grid base that support the tissue culture vials in a vertically upright position and a compatible liquid refrigerant. The supporting grid has holes which receive the vials, and the height of the grid and size of the holes are such as to conveniently accommodate conventional biological tissue culture vials. The volume of liquid refrigerant is at least 15 times the volume of the tissue cultures to be frozen and is filled in the container to a level to totally immerse all of the cultures contained in the upright vials. The preferred liquid refrigerants are straight chain aliphatic alcohols, especially ethanol and methanol. By placing the cell culture vials in the supporting grid, the cultures are automatically immersed in the liquid refrigerant. When the device is placed in a freezer, the liquid refrigerant controls the rate of temperature reduction of the contained cultures at or near the optimum $-1°$ C./min. rate to frozen temperatures of $-30°$ C., and below.

DESCRIPTION OF THE PREFERRED EMBODIMENTS

Generally, the invention is applicable to any live cell culture, especially eucaryotic cell cultures, which is to be cooled to a temperature of about $-30°$ C. or below to preserve cell viability. The cells to which this invention is particularly applicable include the following: epithelial, fibroblastic and lymphoid cell cultures of man, mouse, rabbit, rat, chicken and others.

Figure 1:
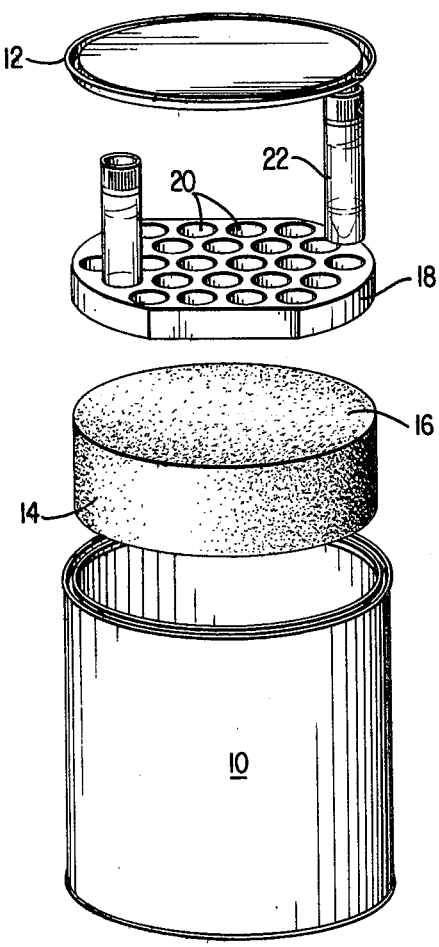
FIG. 1 is an exploded view of the device of this invention showing two culture vials and related holes in the supporting grid.
Figure 2:
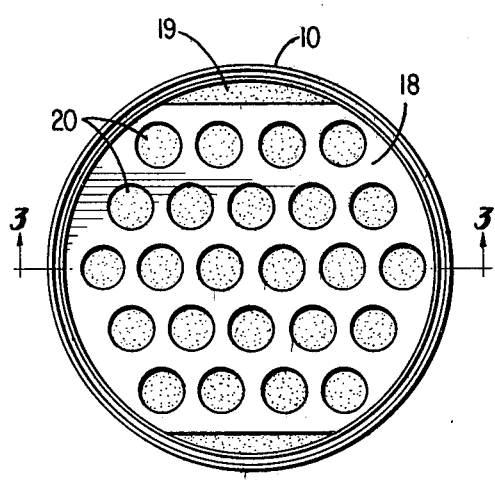
FIG. 2 is a top plan view of the device with the lid removed, showing the interior of the device and before any liquid refrigerant is added.

As shown in FIG. 1, the apparatus of this invention includes a suitable container 10 and closing lid 12. The lid 12 should completely close the container 10. Positioned on the bottom of the container 10 is a supporting grid base 14. This grid base 14 is preferably formed of a sponge-like material, such as foam rubber. As shown, the supporting grid base 14 fits neatly in the bottom of the container 10 and provides a level top surface 16.

Positioned above the supporting grid base 14, and resting on its level top surface 16, is a supporting grid 18. Grid 18 has a series of vertical holes 20 extending therethrough, into which are placed for support individual tissue culture vials 22 containing tissue cultures 24. Portions 19 of the otherwise cylindrical shape of the grid 18 are cut out to facilitate insertion of the grid into the container 10. The vials 22 to be used in this invention are the conventional types in which cell cultures are normally frozen. These include standard plastic freezing vials, presently marketed under the brand name "Nunc", and standard glass ampules.

Liquid refrigerant 26 is added to the container 10 to a level preferably above the top surface 16 of the supporting grid 18, but below the tops of the supported vials 22. The liquid refrigerant 26 must be at a level above the level of each culture 24 to be frozen.

Holes 20 are sized to be slightly larger than the vials 22 supported therein. The diameter of the holes 20 is preferably 1/64" to 1/32" larger than the diameter of the vials 22. Sizing the holes 20 slightly larger than the vials 22 insures that the liquid refrigerant 26 wets the outside of the vials 22 and facilitates insertion and removal of the vials in the grid. The wetting of the outside of the vials is helpful in insuring a relatively uniform temperature reduction at or near the desired optimum level of $-1°$ C./min.

Figure 3:
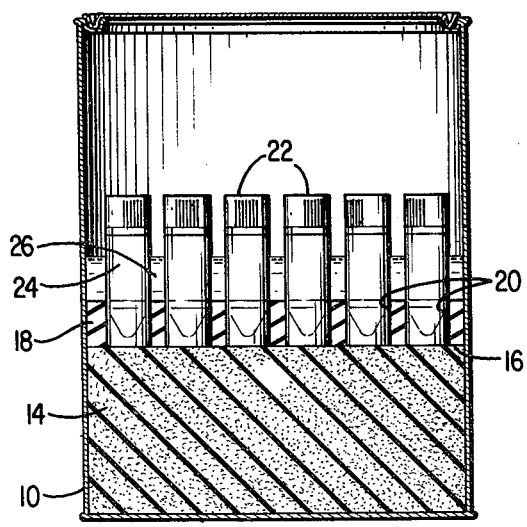
FIG. 3 is a cross-sectional view taken along line 3—3 of FIG. 2, after liquid refrigerant has been added, and six tissue culture vials have been inserted in the supporting grid.

The thickness of the supporting grid 18 should be great enough to support the vials 22 in holes 20 in an upright position, as shown in FIG. 3, but allow a significant portion of the vials 22 to extend above the grid top surface 16 for ready insertion and removal from the grid. Cell culture vials 22 are normally about $1\frac{1}{2}"$ high and it has been found that a $\frac{1}{2}"$ high supporting grid 18 is satisfactory. Any suitable sturdy material can be used for constructing the supporting grid 18, so long as it can withstand temperatures down to $-90°$ C., and is inert in the liquid refrigerant. It is preferable to use a material which has some flexibility down to the $-90°$ C. temperature in order not to cause any damage to the vials 22 during insertion and removal. It has been found that silicone rubber, or natural rubber, are quite suitable. Further, these type materials allow the supporting grid 18 to be made by injection molding.

Utilizing a supporting grid base 14, which is spongelike and therefore both flexible and cellular, such as foam rubber, has two significant advantages. First, it provides space for the liquid refrigerant in a quantity sufficient to insure temperature reduction of the cell culture at or near the desired theoretical optimum, as described hereinafter. And, second, it provides a cushioning base on which the bottom of the vials 22 rest when inserted in holes 20.

It is a critical part of the method of this invention that a certain minimum quantity of liquid refrigerant must be employed in the invented device if proper freezing of the cell cultures is to be accomplished. Tests have demonstrated that there is a critical minimum ratio between the liquid refrigerant volume and the cell culture volume which must be maintained in the container if this invention is to achieve the desired results. In particular, it has been found that the volume of liquid refrigerant 26 must be more than fifteen times the volume of cell cultures 24 present to be frozen. Preferably the ratio should be in the neighborhood of 25:1 to 30:1, or even higher. There is no critical maximum for this ratio except insofar as practical size of the container 10 dictates. Suitable liquid refrigerants are the straight chain aliphatic alcohols, such as methanol, ethanol, propanol, butanol as well as others of longer chain hydrocarbons. Ethanol and methanol are preferred because of their availability at a reasonable cost. Both have been found highly suitable in the present invention when used in volumetric quantities above the critical minimum of 15:1 to the volume of cell cultures to be frozen.

The number of holes 20 in supporting grid 18 is not critical, and can vary from one to a large number, say, in excess of fifty, depending upon the size of the container 10 and the number of vials to be frozen at any particular time by the scientist or technician. It has been found for the purpose of the present invention that a supporting grid containing between five and thirty holes is suitable, and twenty to twenty-five the preferred.

A quart size can has been found suitable for the container 10 and lid 12. A filled quart can normally contains approximately 1000 ml of liquid. In such a container, a foam rubber grid support base 14 approximately $3\frac{1}{4}"$ high is satisfactory and inserted to rest on the bottom. A supporting grid 18, approximately $\frac{1}{2}"$ high with twenty-four holes can be conveniently made, either by injection molding or drilling the holes through a solid piece. It is then inserted in the can to rest on top of the grid support base. With such a construction, it is found desirable to add approximately 750 ml of ethanol (or methanol) which produces a liquid level slightly above the top surface of the grid 18, or approximately 3.75 inches from the bottom of the can, without any vials. As vials are inserted, the level increases slightly. With a supporting grid 18 having 24 holes, sized for standard plastic freezing vials, such as brand "Nunc", placing 4 vials in the grid would provide a liquid refrigerant to cell culture volume ratio of about 60:1. Twenty-one vials in place would give a ratio of about 35:1.

Once the cell cultures have become frozen and the temperature reduced to about $-50°$ C. or below by placement of the device of the instant invention in the laboratory freezer at temperatures of −70° C. or below, it is then safe to transfer the vials containing the frozen cultures to conventional liquid nitrogen storage facilities. While it is not intended that the device of this invention be used to store frozen samples, it will be obvious to those skilled in the art that the device can be used for such storage if other facilities are not available. However, it is preferable to transfer the frozen cultures to established storage facilities so that the apparatus and method of this invention can be used again to freeze other samples.

Temperature versus time tests were conducted using the one quart can device of the instant invention described above. The cell cultures were contained in conventional plastic freezing vials marketed under the brand name "Nunc", and the device was placed in a standard laboratory freezer operated at about −70° C. The results are tabulated in the following table.

TABLE I

| Time (min.) | Temperature (°C.) | | | | | | | |
|---|---|---|---|---|---|---|---|---|
| | P-1 | P-2 | P-2A | P-3 | P-4 | P-4A | P-5 | P-6 |
| 0 | 20.0 | 20.0 | 20 | 20.0 | 20.0 | 20 | 21.0 | 20.0 |
| 5 | 13.0 | 11.0 | 13.5 | 11.5 | 12.0 | 11 | 14.0 | 14.5 |
| 10 | 9.5 | 7.0 | 9.5 | 6.5 | 5.0 | 7 | 10.0 | 11.5 |
| 15 | 6.0 | 3.0 | 7.0 | 2.5 | 1.0 | 1 | 4.5 | 7.5 |
| 20 | 0.0 | −1.0 | 2.5 | −1.0 | 3.5 | −2 | 0 | 2.0 |
| 25 | −4.5 | −5.0 | −1.0 | −6.0 | −8.0 | −10 | −5.0 | −2.0 |
| 30 | −5.0 | −10.0 | −5.5 | −10.0 | −12.5 | −13 | −8.5 | −7.0 |
| 35 | −8.0 | −14.0 | −10 | −14.0 | −17.0 | −17.5 | −12.0 | −11.0 |
| 40 | −15.0 | −18.0 | −12 | −18.0 | −20.5 | −21 | −15.0 | −12.0 |
| 45 | −21.0 | −22.0 | −15 | −22.0 | −24.0 | −25 | −19.5 | −14.0 |
| 50 | −25.5 | −24.0 | −19 | −24.0 | −27.0 | −29 | −23.5 | −17.0 |
| 55 | −29.0 | −26.0 | −23 | −26.5 | −30.0 | −29 | −27.5 | −21.0 |
| 60 | −32.0 | −29.0 | −28 | −30.0 | −32.0 | −32 | −31.0 | −25.0 |
| 65 | −34.5 | −33.0 | −32 | −33.5 | −35.5 | −36 | −35.0 | −29.0 |
| 70 | −36.5 | −36.0 | −35 | −36.5 | −38.0 | −39 | −37.5 | −32.0 |
| 75 | −39.0 | −38.0 | −38 | −39.0 | −40.0 | −42 | −40.0 | −35.0 |
| 80 | −41.0 | −40.0 | −41 | −42.0 | −42.0 | −44 | −43.0 | −38.0 |

Figure 4:
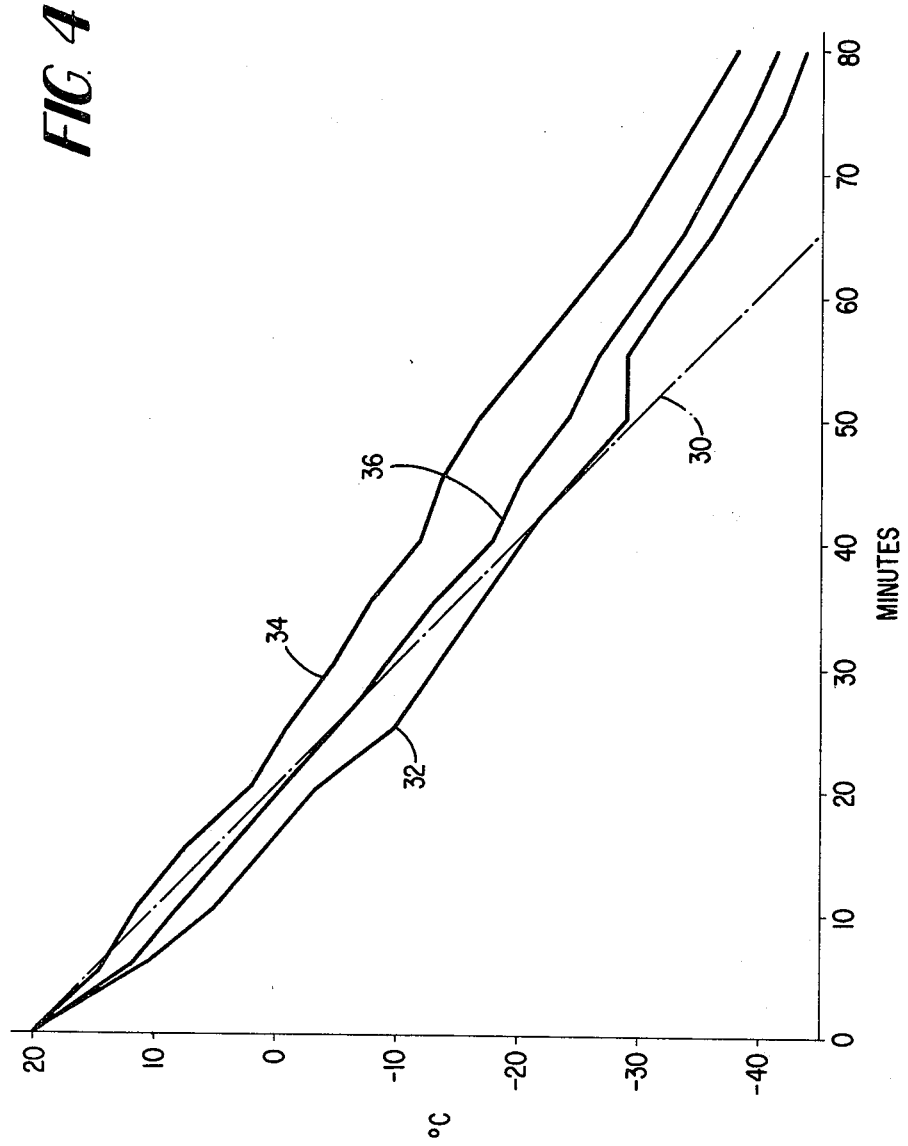
FIG. 4 is a graph plotting the test data contained in Table I.

In each of the runs the temperature of one cell culture sample being frozen was measured at 5 minute intervals. A thermocouple probe was inserted through the top of the can and the top of the vial and extended into the culture. The meter was outside the freezer and the temperature was thus read every 5 minutes. In each of runs P-1, P-2, P-2A and P-6, the liquid refrigerant used was ethanol, and in runs P-3, P-4, P-4A and P-5, the liquid refrigerant used was methanol. In each of the runs, 750 ml of liquid refrigerant was employed and 5 vials of cell culture were inserted in the supporting grid, except in run P-6 where twenty vials were used. The data as shown in Table 1 is compiled in FIG. 4. Line 30 is the desired theoretical optimum, −1° C./min. Curve 32 shows the minimum temperature encountered at each time interval during the eight runs, and curve 34 plots the maximum temperature encountered at each time interval during the eight runs. Finally, curve 36 shows the average temperature at each time interval for the eight experiments. As can be seen, the apparatus of the instant invention produced temperature reductions closely approximating the theoretical optimum from about +10° C. to approximately −30 ° C., and was closest during the critical freezing temperatures of about +5° C. to about −25° C.

Stated another way, the theoretical optimum, i.e., −1° C./min., as illustrated by line 30, is a straight line function. It is believed that any liquid which remains as a liquid from +20° C. to −70° C. and drops in temperature from about +10° C. to about −40° C. in a −70° C. freezer in a substantially linear curve which approximates a temperature decrease of 1° C. per minute, plus or minus about 20%, has the necessary heat transfer capability to perform satisfactorily in the instant invention. However, the liquid must naturally satisfy other criteria, such as inertness, viscosity, etc.

Figure 5:
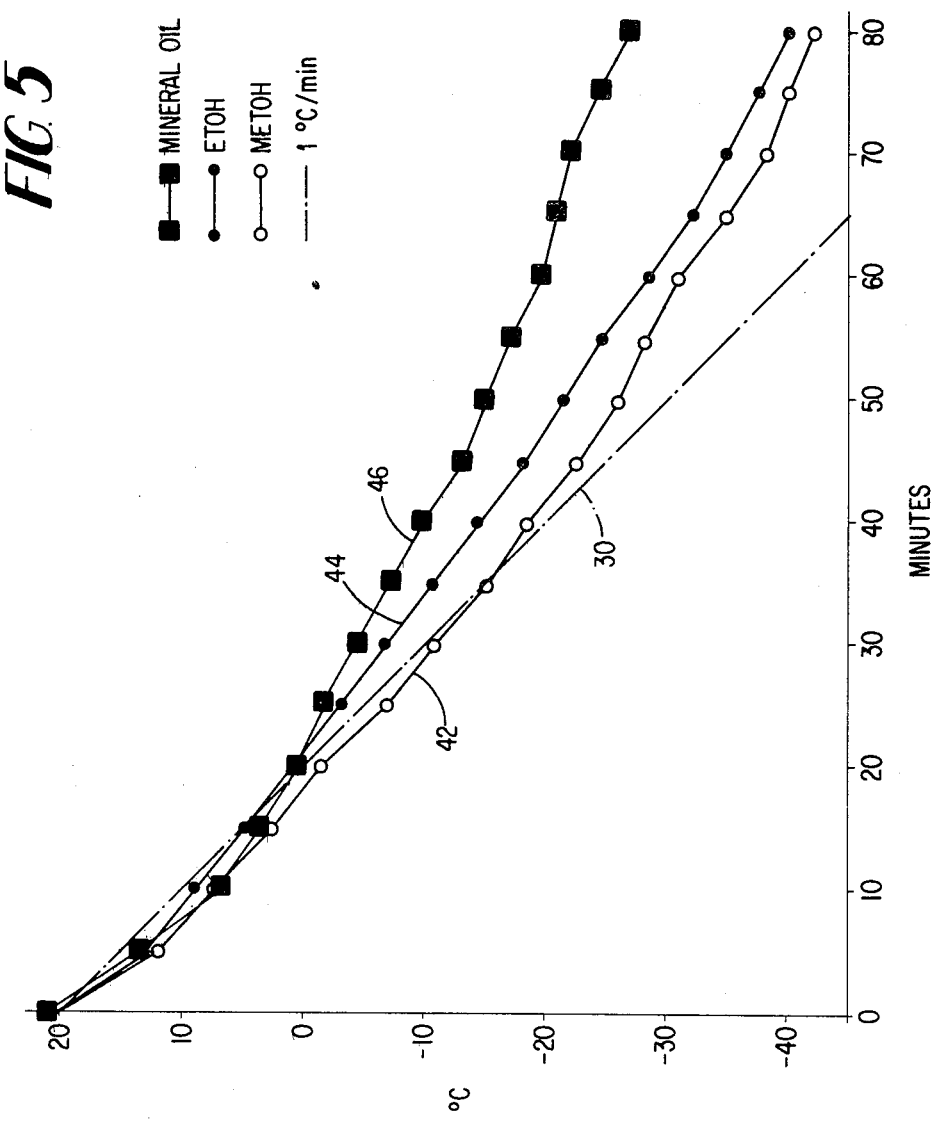
FIG. 5 is a graph plotting the results using the apparatus of this invention with three different liquid refrigerants.

Turning now to FIG. 5, tests were run using the quart can device as explained previously, in which different liquid refrigerants were employed and the temperature of one cell culture sample was measured at five minute intervals in the same manner as previously described in connection with Table I. Line 30 again represents the theoretical optimum −1° C./min. Curve 42 plots the results obtained using a methanol liquid refrigerant, curve 44 plots the results using an ethanol liquid refrigerant, and curve 46 plots the results using mineral oil as the liquid refrigerant. In each test, 750 ml of liquid refrigerant were added to the quart can and 21 cell cultures were frozen during the test. The device was placed in a standard laboratory freezer operated at −70° C. As can be seen from FIG. 5, when the device used either ethanol and methanol a temperature reduction which approximates the theoretical optimum was produced. On the other hand, when employing mineral oil, the temperature reduction is considerably slower and resulting curve 46 depicts a temperature reduction curve which is outside the acceptable limits of the present invention. Mineral oil is also not satisfactory in the present invention because it is too viscous.

Further, tests were conducted to verify the viability of culture cells frozen in accordance with the present invention using the one quart can device described previously. In each case, ethanol was the liquid refrigerant and approximately 750 ml were added. All of the samples listed were frozen with the device placed in a standard freezer of −70° C. Each culture was tested for % viability by standard techniques both before and after freezing. The results were as follows.

TABLE II

| | Sample | % viable cells | |
|---|---|---|---|
| | | Before Freezing | After Freezing |
| rabbit-mouse hybridoma | 1 | 94.3 | 77.6 |
| | 2 | 95.9 | 74.1 |
| | 3 | 91.2 | 80.0 |
| mouse-mouse hybridoma | 1 | 83.2 | 77.8 |
| | 2 | 80.3 | 64.3 |
| | 3 | 74.6 | 71.0 |
| (Epstein - | B95-8 | 99.0 | 84.1 |

TABLE II-continued

|  | Sample | % viable cells | |
|---|---|---|---|
|  |  | Before Freezing | After Freezing |
| Barr virus | NC37 | 94.6 | 91.8 |
| established cell lines) | Raji | 95.5 | 76.9 |
| mouse myeloma cells | 1 | 90.8 | 70.8 |
|  | 2 | 88.7 | 80.1 |
|  | 3 | 100 | 90.9 |

From the foregoing description, one skilled in the art can easily ascertain the essential characteristics of the invention and, without departing from the spirit and scope thereof, can make various changes and modifications to adapt the invention to various stages and conditions.

What is claimed is:

1. A device for controlled freezing of cell cultures contained in a portion of one or more cell culture vials which comprises:
    (a) a container having a removable lid and a bottom;
    (b) grid means for independently supporting each cell culture vial in a substantially upright position in said container;
    (c) a volume of liquid refrigerant in said container sufficient to completely submerse said portion of each vial containing cell culture in said refrigerant, said volume of refrigerant being in excess of fifteen times the total volume of cell culture contained in said one or more vials; and
    (d) suspension means resting on the bottom of said container to suspend said grid means and said one or more vials above the bottom of said container.

2. A device in accordance with claim 1 wherein said container is cylindrical.

3. A device in accordance with claim 1 wherein said grid means has substantially uniform holes completely therethrough, each sized to readily receive a cell culture vial, and said suspension means supports each said vial positioned within a said hole in said supporting grid.

4. A device in accordance with claim 3 wherein said suspension means is formed of a sponge-like material to absorb a portion of the liquid refrigerant in said container and provide a cushioning effect to the bottom of each culture vial supported by said means.

5. A device in accordance with claim 3 wherein said supporting grid contains five to twenty-five holes.

6. The apparatus of claim 3 wherein the size of the holes are sufficiently large compared to the culture vials so that the liquid refrigerant substantially wets that portion of the vial containing the cell culture within the hole.

7. A device in accordance with claim 1 wherein said volume of liquid refrigerant is in excess of twenty-five times the total volume of cell culture.

8. A device in accordance with claim 1 wherein said liquid refrigerant is a straight chain aliphatic alcohol.

9. A device in accordance with claim 8 wherein said liquid refrigerant is selected from the group consisting of ethanol and methanol.

10. A device in accordance with claim 1 wherein said cell cultures comprise eucaryotic cell cultures.

11. A device for controlling the rate of temperature change in a material contained within a portion of one or more test vials which comprises:
    (a) a container having a removable lid and flat bottom;
    (b) a sponge-like base resting on the bottom of said container and having a substantially level top surface;
    (c) a supporting grid resting on said base and positioned within said container;
    (d) a series of substantially vertical holes extending through said grid and sized slightly larger than said vials whereby a vial positioned within a hole will have its bottom resting on the top of said base; and,
    (e) a volume of straight chain aliphatic alcohol in said container sufficient to completely submerse in the refrigerant the portion of each vial containing said material.

12. The device of claim 11 in which the material contained in said vials is tissue cell cultures and the volume of said liquid refrigerant is in excess of fifteen times the total volume of cell cultures contained in said test vials.

13. A device for controlling the rate of temperature change in a material contained within a portion of one or more cylindrical test vials which comprises:
    (a) a container having a removable lid and flat bottom, said container adapted to contain a sufficient volume of refrigerant to completely submerse in the refrigerant the portion of each vial containing said material;
    (b) a sponge-like base resting on the bottom of said container and having a substantially level top surface;
    (c) a supporting grid resting on said base and positioned within said container; and
    (d) a series of substantially vertical cylindrical holes extending through said grid and sized slightly larger than said cylindrical vials whereby a vial positioned within a hole will have its bottom resting on the top of said base.

14. A device in accordance with claim 11, wherein said one or more test vials are of generally cylindrical form, and wherein said substantially vertical holes are cylindrical.

15. A device for controlled freezing of cell cultures contained in a portion of one or more cell culture vials which comprises:
    (a) a container having a removable lid and a bottom;
    (b) grid means for supporting each cell culture vial independently in a substantially upright position in said container;
    (c) suspension means resting on the bottom of said container to suspend said grid means and said one or more vials a sufficient distance above the bottom of said container to define a liquid refrigerant space between the bottom of the container and said cell cultures; and
    (d) said liquid refrigerant space having a volume in excess of approximately 15 times the total volume of cell culture contained in said one or more vials.

* * * * *